United States Patent [19]

Wagner

[11] 4,139,008
[45] Feb. 13, 1979

[54] CONTROLLED-DOSE INJECTION APPARATUS

[76] Inventor: Wolfgang Wagner, Klosterfelder Weg 29, 1 Berlin 27, Fed. Rep. of Germany

[21] Appl. No.: 790,301

[22] Filed: Apr. 25, 1977

Related U.S. Application Data

[63] Continuation-in-part of Ser. No. 634,742, Nov. 21, 1975, abandoned.

[51] Int. Cl.² .............................................. A61M 5/00
[52] U.S. Cl. ................................. 128/215; 128/218 A
[58] Field of Search ................... 128/215, 216, 214 R, 128/214 F, 218 R, 218 A, 218 G, DIG. 1, DIG. 12, 230, 224

[56] References Cited
U.S. PATENT DOCUMENTS

2,703,084  3/1955  Tomlinson ...................... 128/214 F
3,543,752  12/1970  Hesse et al. ...................... 128/230 X
3,848,592  11/1974  Willock ............................ 128/214 R
3,874,826  4/1975  Lundquist et al. ........... 128/DIG. 12
3,949,746  4/1976  Wallach ...................... 128/218 A X
3,994,294  11/1976  Knute .............................. 128/214 F

Primary Examiner—John D. Yasko
Attorney, Agent, or Firm—Michael J. Striker

[57] ABSTRACT

An injection apparatus has a medicament container whose hollow interior is subdivided by a partition into a medicament compartment housing a body of the liquid medicament and a pressurizable compartment. A positive-displacement pump has an intake connected via a conduit to the medicament compartment and is operable to pass a liquid from this intake to its output. A needle is provided on the output so that when implanted in a person this pump can be used to inject a predetermined carefully metered quantity of the medicament into the person.

9 Claims, 16 Drawing Figures

CONTROLLED-DOSE INJECTION APPARATUS

CROSS-REFERENCE TO RELATED APPLICATIONS

This application is a continuation-in-part of my copending application Ser. No. 634,742 filed 21 Nov. 1975 now abandoned and whose entire disclosure is herewith incorporated by reference. This application is also related to my copending patent applications Ser. Nos. 639,685 filed 25 Dec. 1975, 634,741 filed 21 Nov. 1975, and 639,685 filed 8 Dec. 1975, all now abandoned and all of whose disclosures are also herewith incorporated by reference.

BACKGROUND OF THE INVENTION

The present invention relates to an injecting apparatus. More particularly this invention concerns an apparatus for hypodermic injections wherein a plurality of different liquid medicaments can be used in a single apparatus and/or a plurality of injections with measured doses can be performed seriatim.

A hypodermic injection, whether intravenous, subcutaneous, or intramuscular, has traditionally been carried out by means of a standard hypodermic syringe. This device comprises a hollow tube provided at one end with a needle and provided internally with a piston. A plunger forces the piston forward, thereby decreasing the volume of the interior of the tube and forcing a liquid medicament through the hollow needle. Such an arrangement usually has limited holding capacity so that it must be refilled if a series of injections is to be performed with it, and exact dosing of the injections is difficult.

Various other devices are known, such as described in U.S. Pat. Nos. 2,960,087, 3,727,614, and 3,827,601 as well as in German Auslegeschrift 1,491,840. These arrangements are all relatively complex gas-powered devices serving for hypodermic injection. They are all relatively complex and, therefore, expensive devices. What is more in these arrangements the medicament is exposed to air so that the devices cannot be used with any medicament that would readily be damaged or oxidized by air, and cannot be laid up for a long time as the medicament therein will dry out. Furthermore, these arrangements all rely on relatively complex piston-type dosing arrangements which have been found to be relatively failure prone and difficult to clean. Finally, the change over in these arrangements from one liquid medicament to another normally requires almost complete disassembly of the units and sterilizing in an autoclave.

SUMMARY OF THE INVENTION

It is therefore an object of the present invention to provide an improved hypodermic injecting apparatus.

An another object is to provide such an apparatus which is relatively simple and which can be produced at relatively low cost.

A further object is to provide an injecting apparatus which can easily be cleaned, and which also can be used with several different medicaments without difficulty.

These objects are attained according to the present invention in an apparatus comprising a medicament container having a hollow interior adapted to contain a body of a liquid medicament. A positive-displacement pump having an intake and an output and operable to pass a liquid from the intake to the output has its intake connected via a conduit to the medicament container. Means is provided for forcing the medicament from the container through the conduit to the pump intake. A hollow injecting needle is connected to the output and means is provided for operating the pump and thereby feeding a predetermined quantity of the medicament to the needle. Thus, when the needle is pierced into a patient the quantity the liquid medicament can be injected into the patient. The interior of the medicament container is subdivided by a partition into a medicament compartment holding the body of medicament and a pressurizable compartment. The means for forcing the medicament through the conduit includes means for pressurizing the pressurizable compartment and thereby forcing the partition to move in such a manner that the volume of the medicament compartment decreases and that of the pressurizable compartment increases.

Thus with the present invention a relatively simple and highly accurate dosing pump is employed to meter the desired quantity of the liquid medicament to the needle. Furthermore, the separation of the interior of the medicament container into a pair of separate compartments by means of the partition prevents the gaseous propellant that serves to pressurize the medicament from contacting this medicament and contaminating it, drying it out, or otherwise adversely affecting it.

In accordance with further features of this invention means is provided in the partition for plugging the upstream end of the conduit leading to the metering pump. This means may be a plug which is mounted on the partition in such a manner that when the partition moves all the way up to the end of the container into a position wherein the medicament is largely exhausted, the plug will fit into the upstream end of the conduit. Thus operation of the device so as to draw in air, which could potentially be very dangerous for the patient, is ruled out.

According to yet another feature of this invention means is provided for flushing out the container and/or the conduit and/or the needle and pump. Thus without disassembling the entire arrangement it is possible to flush any traces of medicament from it and use it with another medicament without danger of contamination.

The needle according to this invention may have its outer end provided with a suction arrangement that is particularly useful for intravenous injections so as to insure that the inner end of the needle is properly placed within a vein. This suction means is associated with another plug which is so set up as automatically to prevent further suction and open the needle up for feed from the dosing pump once the needle has drawn in some blood to indicate its proper placement. Thus an actuating element on the replaceable needle part is operated when the suction means has drawn in some blood so as first to stop the suction means from aspirating through the needle, thereafter to open up the outer end of the needle for flow from the dosing pump, and thereafter to open a valve at the output of the dosing pump for a metered discharge of the desired quantity of liquid medicament through the needle into the patient.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

SPECIFIC DESCRIPTION OF PREFERRED EMBODIMENTS

Figures 1, 2, 3:
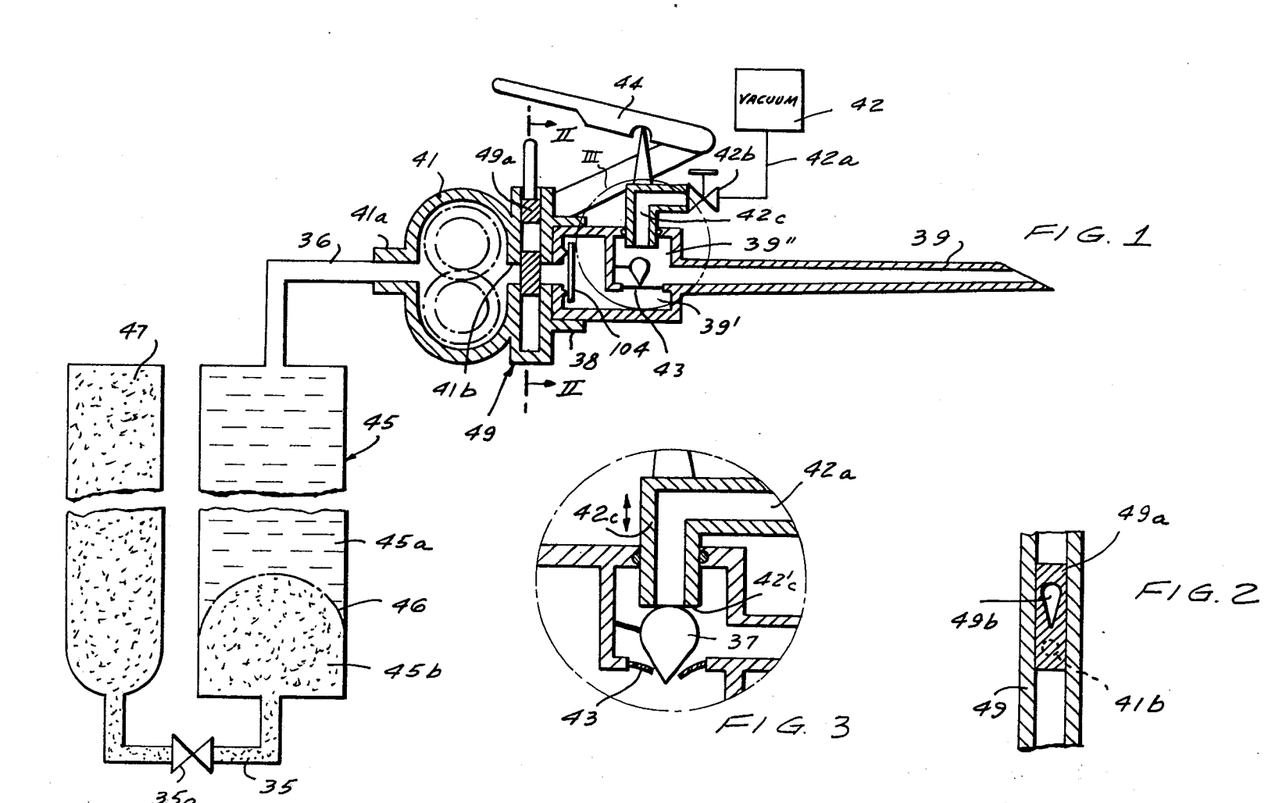
FIG. 1 is a partly diagrammatic axial section through an injecting apparatus according to this invention.
FIG. 2 is a section taken along line II—II of FIG. 1.
FIG. 3 is a large-scale view of a detail of FIG. 1.

As shown in FIGS. 1 - 3 an apparatus for intravenous injection has a hollow needle 39 whose one end is pointed and whose other end is widened and connected via a bayonet coupling 38 to a valve 49. This last-mentioned end of the needle 39 is subdivided into a pair of compartments 39' and 39" separated by a frangible membrane 43 that is associated with a pivotal pointed plug 37. A vacuum source 42 has a conduit 42a in which is provided a valve 42b and has an inner end 42c which extends into the compartment 39" and which has an end 42c' blockable by means of the rounded back end of the plug 37. This inner end 42c is displaceable toward and away from the plug 37 by means of a lever 44. Thus when the lever 44 is pivoted downwardly as seen in FIG. 1 the end 42c will first come into snug engagement with the plug 37 so as to stop suction through the conduit 42a and thereafter the plug 37 will have its pointed end forced through the membrane 43 so as to permit fluid flow between the compartments 39' and 39".

A gear-type pump 41 has an intake 41a connected via a conduit 36 to a container 45 subdivided by means of a flexible membrane 46 into a medicament compartment 45a and a pressurizable compartment 45b, the former being connected to the conduit 36 and the latter being connected via a conduit 35 having a valve 35a to a pressurized gas bottle 47.

The pump 41 has an output 41b at which is provided a valve 49 having a slider 49a formed with a hole alignable with the output 41b so as to permit liquid flow from the pump 41 into the compartment 39'. A flap-type check valve 104 is provided in the compartment 39' so that liquid can only enter this compartment 39' but cannot exit therefrom back into the pump 41.

Figure 4:
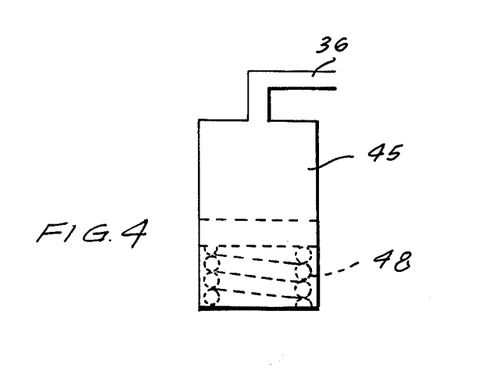
FIG. 4 is a detail view of an alternative arrangement according to this invention.

It is noted that the gas bottle 47 and conduit 45 constituting means for forcing a liquid medicament in the compartment 45a through the conduit 36 to the pump 41 can be replaced by a simple spring 48 as shown in FIG. 4.

For use a needle 39 is fitted via the bayonet coupling 38 to the valve 49. Thereafter the combined pressurization of the compartment 45b plus operation of the pump 41 will fill the compartment 39'. The tip of the needle 39 is then pierced into the patient, and when a vein is properly reached, the transparent tube 42c will show that some blood has been drawn into the assembly. Thereupon the lever 44 is depressed so as to stop aspiration of the needle 39 and simultaneously rupture the membrane 43 so that medicament can pass between the compartments 39' and 39". Further depression of the lever 44 will move the slider 49a down so that its hole 49b will align with the hole 41b and allow the pump to force the exactly needed quantity of medicament through the needle 39 into the patient. The opening 49b has a width transverse to its direction of displacement which increases in the direction of displacement so that as the slider 49a is pushed down the flow will increase regularly to a predetermined maximum.

Figure 5:
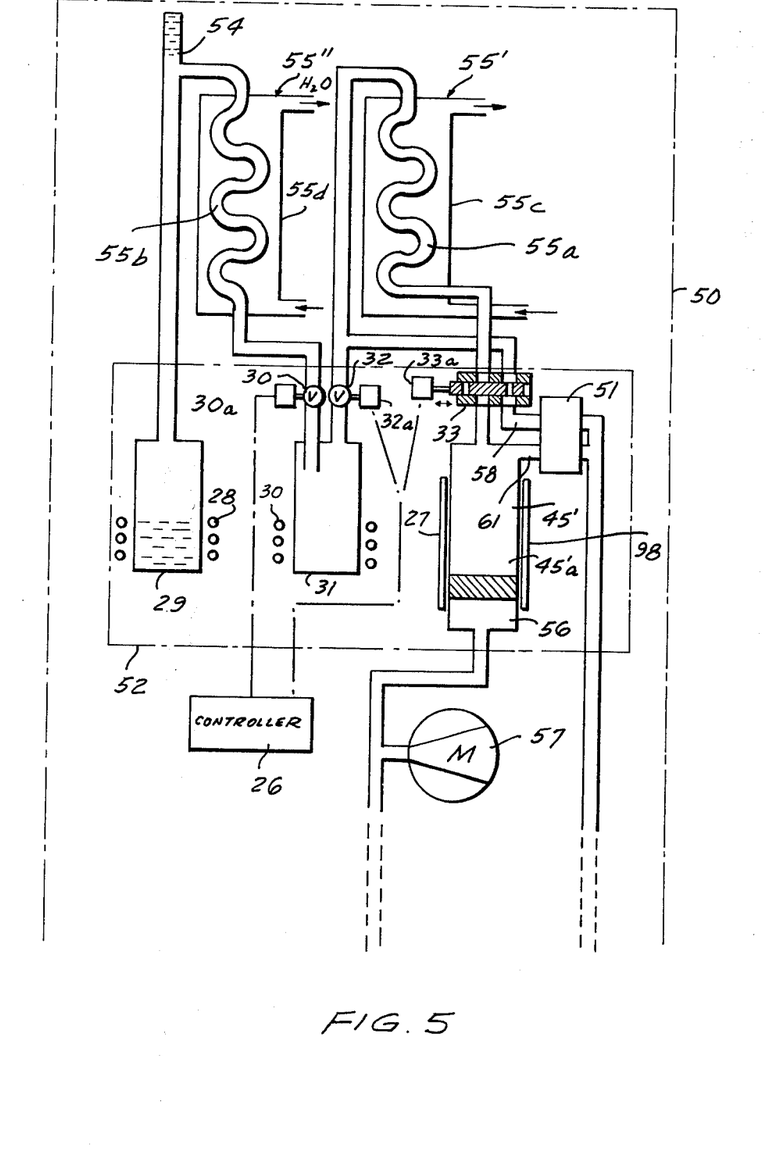
FIG. 5 is a largely schematic view of a flushing arrangement for the injecting apparatus in accordance with this invention.

FIG. 5 shows an arrangement wherein a medicament container 45' has a pressurizable compartment 56 equivalent to the compartment 45b but separated by means of a piston 34 from the medicament compartment. A compressor 57 is used to pressurize this compartment 56. The medicament compartment 45a' of this container 45' has a first outlet connectable via a valve 33 controlled by a solenoid 33a to a distilling coil 55a of one of two distillers 55' and 55". The other end of the coil 55a is connected via a valve 32 controlled by a respective solenoid 32a to a boiler bottle 31 having a heater 30 and another outlet connected through a valve 30 having a respective solenoid 30a to another distilling coil 55b of the other distiller 55". The other end of this coil 55b is in turn connected to a fresh-water inlet 54 and to another boiling vessel 29 having a respective heater 28. The above-mentioned structure is all held in a common housing 50 provided with a thermostatically controlled cooling apparatus connected to a cooling coil 28 for the vessel 45', and having the distillation apparatus 52. Cold water is passed in jackets 55c and 55d around the coils 55a and 55b.

It is therefore possible to admit water to the vessel 29 from the water inlet 54, and boil this water up so that it is distilled the first time through the distiller 55". A controller 26 connected to the various valves and the cooling apparatus, as well as to the pump 41 and compressor 57, opens the valve 30a for this procedure so that the once-distilled water can be drawn into the boiler 31. Thereafter the valve 30 is closed and the valve 32 opened, while the valve 33 is slid to the right as shown in FIG. 5 so that the water in the vessel 31 can be distilled again through the boiler 55'. This water, therefore, can be used to flush from the compartment 45a' any traces of medicament therein.

Figure 6:
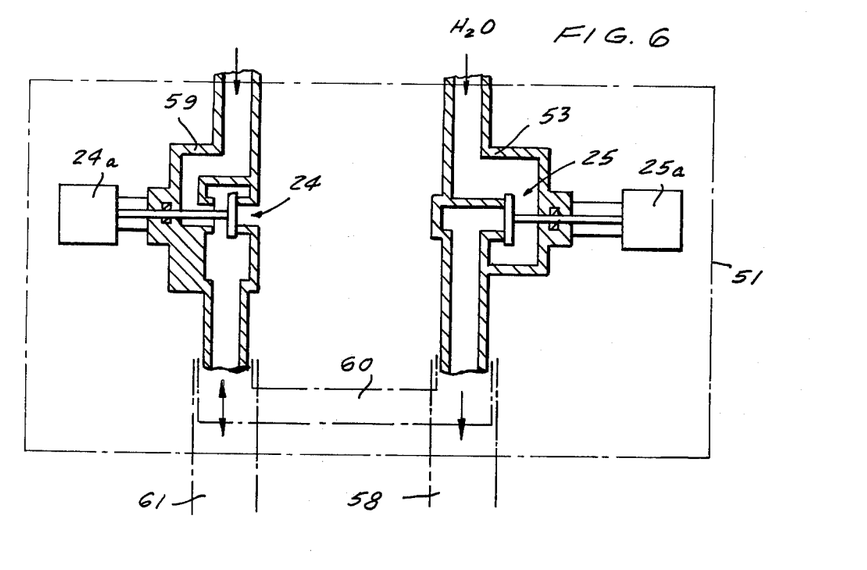
FIG. 6 is a diagrammatic view of another flushing arrangement in accordance with this invention.

Furthermore, the piston 34 can serve to force the distilled water through a valve arrangement 51 shown in FIG. 6. This arrangement comprises a water tube 58 connected to the distiller 55' at the upstream end of the coil 55a thereof, and another conduit 61 connected to the interior of the vessel 45'. Under normal circumstances a pair of solenoid valves 25 and 24 in the lines 58 and 61, respectively, are in the illustrated positions so that flow is possible through the line 61 but not through the line 58. The controller 26 is connected to both of the solenoids 24a and 25a of the valves 24 and 25 so as to move them from the position illustrated in FIG. 5 into a position wherein liquid can pass through the line 58 and through a jumper tube 60 back into the vessel 45' to flush it out as described above.

Figure 7:
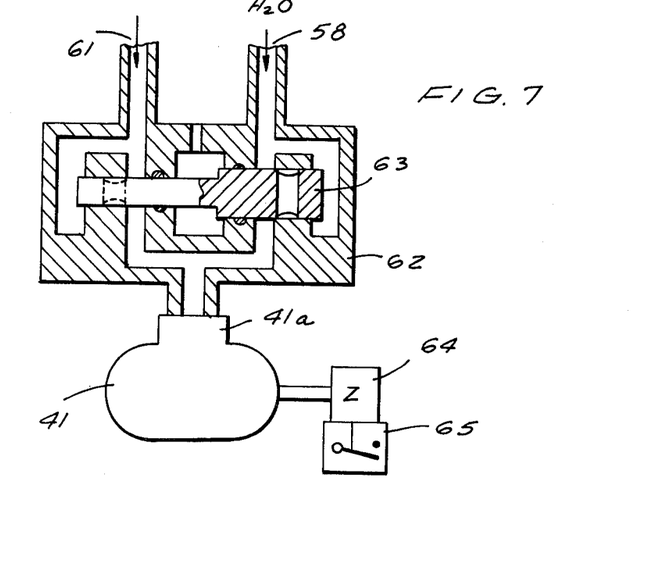
FIG. 7 shows largely diagrammatically a double-check valve for a conduit flusher in accordance with this invention.

FIG. 7 shows a two-way priority check valve 62 connected between the lines 58 and 61 the intake 41a of the pump 41. This double check valve 62 has a slider 63 whose effective surface area exposed to the pressure in the conduit 58 is greater than that exposed to the pressure in the conduit 61 so that when the conduit 58 is pressurized this slider will move to the left in FIG. 7 and block flow through the conduit 61 while allowing steam or water to flow through the conduit 68 into the pump 41 so as to flush it out also.

The pump 41 is associated with a counter 64 having a switch 65 that is actuated each time a predetermined quantity of liquid is passed through the pump 41 for exact metering of the medicament thereby.

Thus operation of the various valves described above allows the entire system to be flushed out with steam and/or hot water. No disassembly of the device is required for such flushing out so that medicament can easily be changed.

Figure 8:
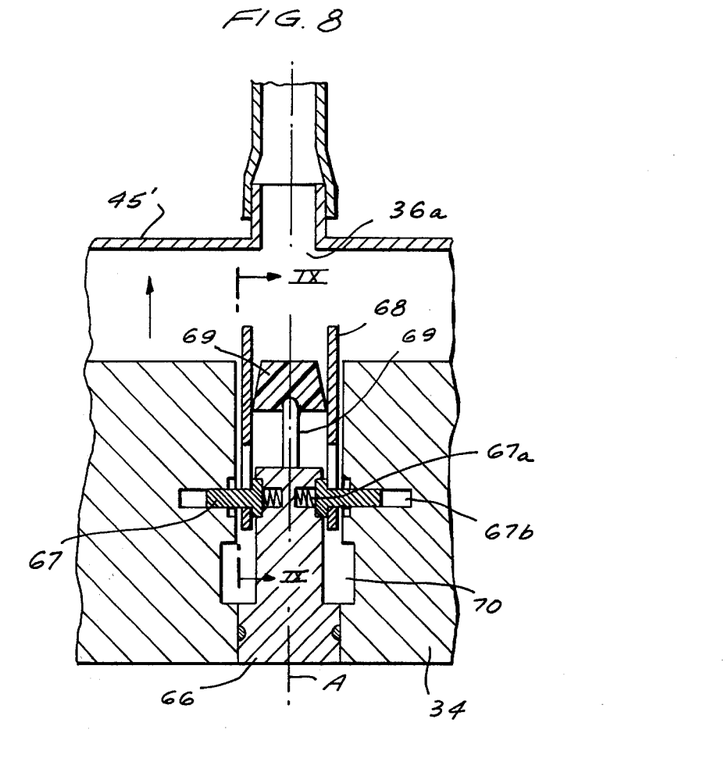
FIG. 8 is a large-scale view of a detail of FIG. 5.
Figure 9:
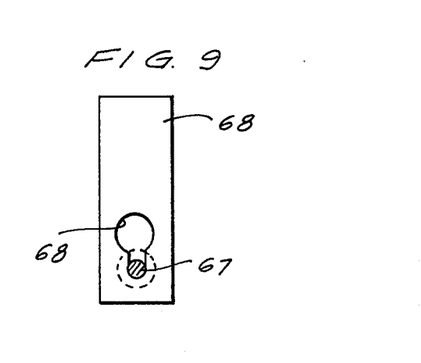
FIG. 9 is a view taken along line IX — IX of FIG. 8.

In FIG. 8 an arrangement is shown which is mounted in the piston 34 of the vessel 45 or 45'. This arrangement basically comprises a plug 69 snugly engageable in the downstream end 36a of the conduit leading away from the vessel 45'. This plug 69 is carried on a stem 69a of a slider-piston 66 that is normally locked in place in the piston 34 by means of a pair of laterally slidable T-shaped pins 67 urged by respective strings 67a outwardly in respective slots 67b formed in the piston 34. Locking slides 68 formed with respective key-hole shaped holes 68a normally prevent the springs 67a from pushing the blocking pins 67 out and thereby freeing the plug 69 for movement relative to the piston 34 along its axis A.

When, however, the piston 34 comes to the end of the vessel 45' the slides 68 will strike the vessel and move backwardly, thereby freeing the pins 67 so that their springs 67a can push them out, in turn freeing the piston 66. Thus, the pressure behind the piston 66 and the piston 34 and in the region 70 will force the piston 66 and thereby the plug 69 forwardly. This plug 69 will wedge itself in the upstream end 36a and prevent any further fluid flow of any kind out of the container 45'.

Such an arrangement insures that once the liquid medicament is used up the device cannot be accidentally employed so as to inject air into a patient.

Figure 10:
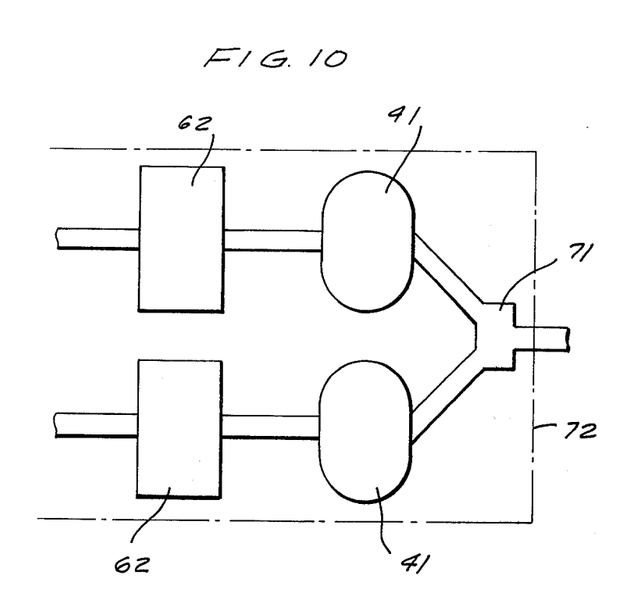
FIG. 10 is a view of a detail of another arrangement in accordance with this invention.

FIG. 10 shows an arrangement wherein a pair of the pumps 41 with their respective valve 62 are connected together at a union 71 in a common housing 72. Such an arrangement allows two separate medicaments to be simultaneously injected with the same apparatus.

Figure 11:
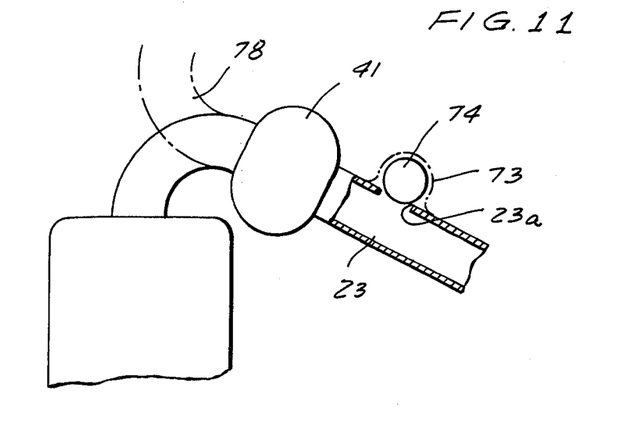
FIG. 11 shows an alternative pump arrangement according to the present invention.

In FIG. 11 an arrangement is shown wherein the dosing pump 41 has its output connected to a conduit 23 whose wall is formed with a throughgoing hole 23a covered by a flexible membrane in which is provided an elastic ball 74. After using up the medicament in the supply container the ball 74 can be pushed through the hole 23a into the tube 23. Then the pump 41 is connected via a line 28 to a source of water so that the ball separates the medicine and the water. In this manner a medicine supply dose can be dosed without a supply container over the needle, a useful feature when small amounts of the medicament are employed as the water on the other side of the ball 74 then serves to advance the medicament while the ball 74 separates the water and the medicament.

Figure 12:
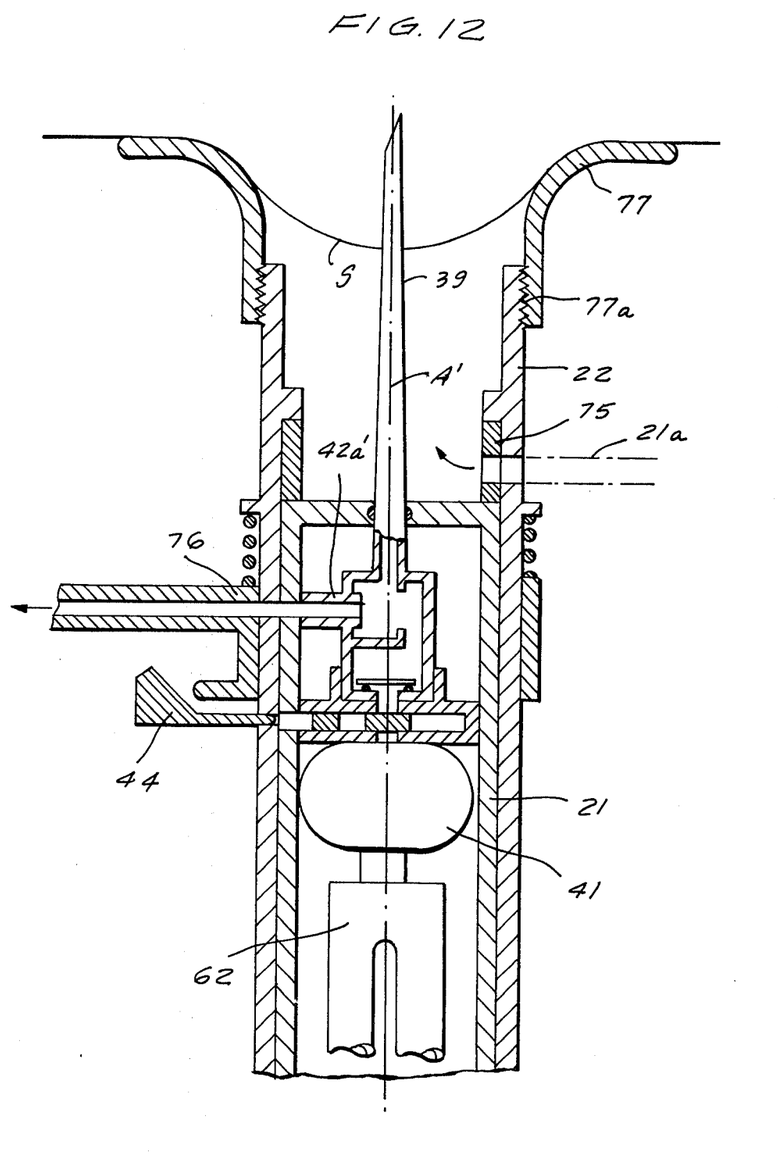
FIG. 12 is a large-scale sectional view through a suction-type injector according to this invention.

In FIG. 12 a suction-type injector is shown having an outer tube 22 on whose one end is threaded a T-shaped muzzle 77 and in which is carried another tube 21 carrying the needle 39 and enclosing the pump 41 and valve 62. The inner sleeve 21 can be moved by suction through a line 21a connected to a sliding sleeve 75 inside the outer cylinder 22. This suction also can pull up the skin S of a person to be injected in a bulge as indicated so that the skin is pulled up toward the needle 39 which will then pierce into it. Once the needle 39 engages into the skin vacuum is stopped. A guide groove prevents turning of the arrangement about its axis A'.

Once pulled into this position a suction hose 76 is aligned with the lateral opening 42a' in the rear end of the needle 39. Otherwise the device functions in a similar manner to that of FIG. 3. Here it is noted, however, that the suction from the line 21 serves for most of the operation of the device, automatically piercing the needle 39 into the skin and moving it into the proper position from a position lower than that shown in FIG. 12 where it is shielded inside the tube 22.

Figure 13:
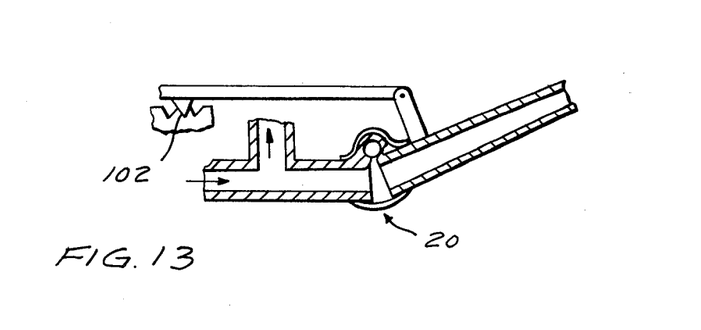
FIGS. 13 and 14 are sectional views through details of constructional alternatives in accordance with this invention.
Figure 14:
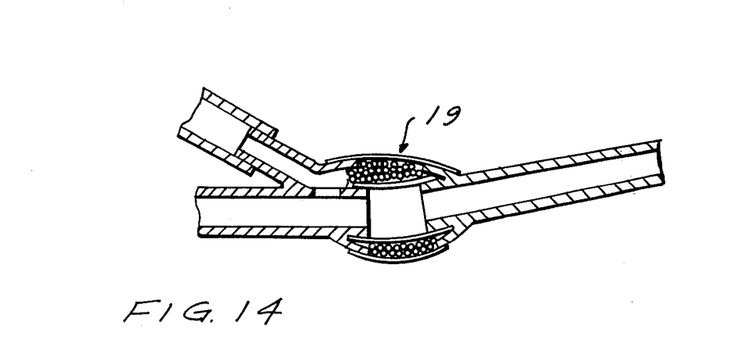

FIGS. 13 and 14 show how a conduit or needle can be made bendable at points 20, and 19. Cuffs are provided along these joints so as to maintain the seal and an adjustment arrangement 102 is provided in the arrangement of FIG. 13 for fixing the one end of the conduit or needle in the desired position relative to the other end.

Figure 15:
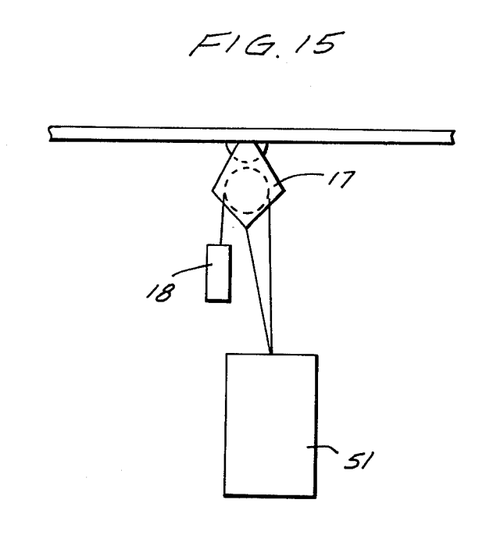
FIGS. 15 and 16 show arrangement for mounting the assembly according to this invention.
Figure 16:
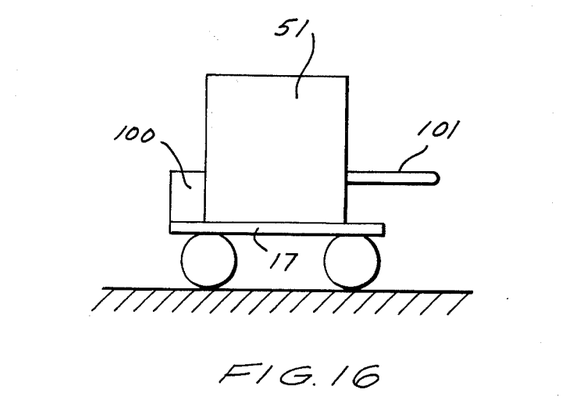

FIG. 15 shows how the arrangement 51 can be mounted on a rail 99 with a counterweight 18 operating via a pulley 17 to maintain it at a desired height. Alternately a cart 17 having a handle 101 and a receptacle 100 for used syringes may be provided for the housing 51 of the arrangement as shown in FIG. 16.

It will be understood that each of the elements described above, or two or more together, may also find a useful application in other types of apparatus differing from the types described above.

While the invention has been illustrated and described as embodied in an injection device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that from the standpoint of prior art, fairly constitute essential characteristics of the generic or specific aspects of this invention.

What is claimed as new and desired to be protected by Letters Patent is set forth in the appended claims.

1. An injecting apparatus comprising a medicament container having a hollow interior adapted to contain a body of a liquid medicament; a positive-displacement pump having an intake and an output and operable to pass a liquid from said intake to said output; a conduit connecting said intake to said container; means for forcing said medicament through said conduit from said container to said intake; a hollow injecting needle connected to said output; means for operating said pump and thereby feeding a predetermined quantity of said medicament to said needle, whereby when said needle is implanted in a patient said quantity is injected into such patient; and a partition subdividing said interior into a medicament compartment holding said body of medicament and a pressurizable compartment, said partition being movable in said container to increase the volume of said pressurizable compartment and decrease the volume of said medicament compartment, said means for forcing including means for pressurizing said pressurizable compartments with a gas.

2. The injecting apparatus defined in claim 1 wherein said partition is a membrane.

3. The injecting apparatus defined in claim 1 wherein said partition is a piston and is provided with means for plugging said conduit when the volume of said medicament compartment has been reduced beyond a predetermined minimum.

4. The injecting apparatus defined in claim 3 wherein said conduit has an upstream end opening into said medicament compartment, said means for plugging including a plug snugly fittable in said upstream end and means on said piston for fitting said plug into said upstream end when said predetermined minimum is passed.

5. The injecting apparatus defined in claim 1, further comprising means for flushing said container with a rinse liquid and thereby eliminating traces of said medicament therefrom, said means for flushing including means for heating said rinse liquid.

6. The injecting apparatus defined in claim 1, further comprising means for flushing said pump and needle with a rinse liquid and thereby eliminating traces of said medicament therefrom.

7. The injecting apparatus defined in claim 1, further comprising a closable valve at said output.

8. The injecting apparatus defined in claim 7, further comprising means for aspirating fluid from inside said needle and means for preventing such aspiration when said medicament is fed through said conduit.

9. The injecting apparatus defined in claim 8 wherein said means for aspirating has a suction inlet in said needle and said means for preventing includes a valve element snugly engageable with said suction inlet to plug same.

* * * * *